(12) United States Patent
Pascal et al.

(10) Patent No.: US 6,803,380 B1
(45) Date of Patent: Oct. 12, 2004

(54) 5-ARYL-1H-1,2,4-TRIAZOLE COMPOUNDS AS INHIBITORS OF CYCLOOXYGENASE-2 AND PHARMACEUTICAL COMPOSITIONS CONTAINING THEM

(75) Inventors: Jean-Claude Pascal, Nice (FR); Denis Carniato, Cagnes sur Mer (FR)

(73) Assignee: Laboratoire Theramex (MC)

( * ) Notice: Subject to any disclaimer, the term of this patent is extended or adjusted under 35 U.S.C. 154(b) by 0 days.

(21) Appl. No.: 10/111,424

(22) PCT Filed: Nov. 6, 2000

(86) PCT No.: PCT/EP00/10956

§ 371 (c)(1),
(2), (4) Date: May 17, 2002

(87) PCT Pub. No.: WO01/34577

PCT Pub. Date: May 17, 2001

(30) Foreign Application Priority Data

Nov. 9, 1999 (EP) ............................................. 99402784

(51) Int. Cl.$^7$ .................... C07D 31/4196; C07D 249/08
(52) U.S. Cl. ................. 514/383; 548/267.2; 548/267.4; 548/267.6; 548/267.8; 548/268.6
(58) Field of Search ....................... 514/383; 548/267.2, 548/267.4, 267.6, 267.8, 268.6

(56) References Cited

U.S. PATENT DOCUMENTS 5,318,959 A * 6/1994 Ozaki et al. .................. 514/63

FOREIGN PATENT DOCUMENTS

| | | |
|---|---|---|
| EP | 572142 | 12/1993 |
| JP | 07/076577 | 3/1995 |
| WO | 95/00501 | 1/1995 |
| WO | 95/15318 | 6/1995 |

OTHER PUBLICATIONS

Tsuji et al, "Studies on Anti–Inflammatory, etc" Chem. Pharm. Bull. 45(6), 987–995 (1997).*
Tsuji et al, Chem. & Pharm. Bull., Pharm. Soc. of Japan, vol. 45, No. 6, pp. 987–995, Jun. 1997.

* cited by examiner

Primary Examiner—Patricia L. Morris
(74) Attorney, Agent, or Firm—Dennison, Schultz, Dougherty & MacDonald

(57) ABSTRACT

5-aryl-1H-triazole compounds of the formula

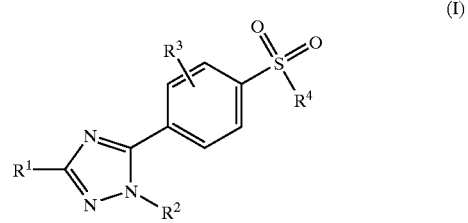

are potent and selective COX-2 inhibitors. The invention further relates to pharmaceutical compositions containing these compounds.

27 Claims, No Drawings

5-ARYL-1H-1,2,4-TRIAZOLE COMPOUNDS AS INHIBITORS OF CYCLOOXYGENASE-2 AND PHARMACEUTICAL COMPOSITIONS CONTAINING THEM

This application is a 371 of PCT/EP00/10956 filed on Nov. 6, 2000.

The present invention relates to 5-aryl-1H-1,2,4-triazole compounds, to a process for their preparation and to pharmaceutical compositions containing them.

Non-steroidal antiinflammatory drugs (NSAIDs) exert most of their effects through inhibition of prostaglandin H synthase (PGHS), which mediates the conversion of arachidonic acid to prostaglandins. The first committed step in this process is the oxidative cyclisation of arachidonic acid to $PGE_2$, which is followed by peroxide reduction to $PGH_2$ at a second distinct binding site. PGHS, commonly known as cyclooxygenase or COX, exist as two isoforms, each with a distinct physiological role (Hla, T et al, Proc. Natl. Acad. Sci. USA. 1992, 89, 7384, Holtzman, H. J. et al, J. Biol. Chem 1992, 267, 21438; Herschman, H. R., Cancer Metastasis Rev. 1994, 13, 241). One isoform, COX-1, is constitutively produced in a variety of tissues and appears to be important in the maintenance of normal physiological functions including renal blood flow and gastric cytoprotection. The second isoform, COX-2, is induced by a variety of inflammatory stimuli and appears to be largely responsible for the high-level production of prostaglandins that results in inflammation (Masferrer, J. L. et al., Proc. Natl. Acad. Sci. USA 1994, 91, 3228; Vane, J. et al. Proc. Natl. Acad. Sci. USA. 1994, 91, 2046).

WO95/15318, WO95/15316, U.S. Pat. Nos. 5,434,178, 5,466,823, 5,504,215, 5,508,426 and 5,510,496 describe 1,5-diaryl-pyrazoles with in vitro and in vivo activities.

Some 1,5-diphenyl-1H-1,2,4-triazoles such as compound (a), having a moderate Cox-2 inhibitory activity and anti-inflammatory potency, which are not superior to that of known anti-inflammatory agents, have been described in Monatshefte fur Chemie 119, 349–353 (1998).

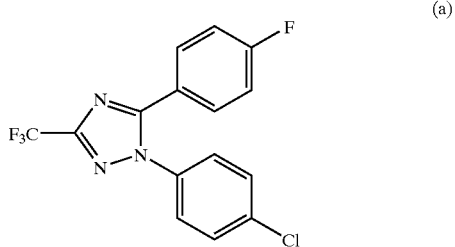

(a)

3-cyano-1,5-diphenyl-1H-1,2,4-triazoles such as compound (b) reported in Chem. Pharm. Bull. 45(6), 987–995 (1997) are weak and non selective inhibitors of cyclooxygenase-1 and cyclooxygenase-2.

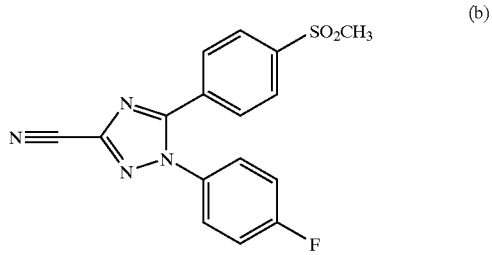

(b)

It has now been found that some 5-aryl-1H-1,2,4-triazole compounds are surprisingly particularly selective and strong inhibitors of cyclooxygenase-2.

Accordingly one object of this invention is to provide 5-aryl-1H-1,2,4-triazole compounds, which have a potent and selective COX-2 inhibiting activity.

The 5-phenyl-1H-1,2,4-triazole compounds of this invention are represented by the following general formula (I):

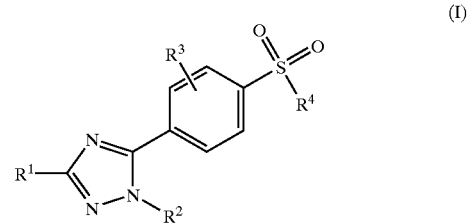

(I)

in which:

$R^1$ is hydrogen; a $(C_1-C_6)$alkyl; a halo$(C_1-C_6)$alkyl; or a phenyl optionally substituted by one or several subsdtients selected from the group consisting of a $(C_1-C_4)$alkyl, a halogen, a halo$(C_1-C_4)$alkyl, a hydroxy, a $(C_1-C_4)$alkoxy, an amino, a mono- or di-$(C_1-C_4)$alkylamino, a $(C_1-C_4)$alkylcarbonylamino, a $(C_1-C_4)$alkylthiocarbonylamino, a $(C_1-C_4)$alkoxycarbonylamino, a $(C_1-C_4)$akoxythiocarbonylamino, a $(C_1-C_4)$alkylsulfonyl, a $(C_1-C_4)$alkylsulfonylamino, a methylenedioxy, a nitro and a cyano;

$R^2$ is a $(C_1-C_6)$alkyl; a $(C_3-C_8)$cycloalkyl; a phenyl or a phenyl$(C_1-C_4)$alkyl in which the phenyl is optionally substituted by one or several substituents selected from the group consisting of a $(C_1-C_6)$alkyl, a halogen, a halo$(C_1-C_4)$alkyl, a hydroxy, a $(C_1-C_4)$alkoxy, an amino, a mono- or di-$(C_1-C_4)$alkylamino, a $(C_1-C_4)$alkylcarbonylamino, a $(C_1-C_4)$alkylthiocarbonylamino, a $(C_1-C_4)$alkoxycarbonylamino, a $(C_1-C_4)$alkoxythiocarbonylamino, a $(C_1-C_4)$alkylsulfonyl, a $(C_1-C_4)$alkylsulfonylamino, a methylenedioxy, a nitro and a cyano; or a heteroaromatic radical;

$R^3$ is hydrogen; a halogen; a hydroxy; a $(C_1-C_6)$alkoxy; an amino; a mono- or di-$(C_1-C_6)$alkylamino; a $(C_1-C_6)$alkylcarbonylamino; a $(C_1-C_6)$alkylthiocarbonylamino; a $(C_1-C_6)$alkoxycarbonylamino; a $(C_1-C_6)$alkoxythiocarbonylamino; a nitro; or a cyano;

$R^4$ is a $(C_1-C_6)$alkyl; an amino; a mono- or di-$(C_1-C_6)$alkylamino; a $(C_1-C_6)$alkylcarbonylamino; a $(C_1-C_6)$alkylthiocarbonylamino; a $(C_1-C_6)$alkoxycarbonylamino; or a $(C_1-C_6)$alkoxythiocarbonylamino; and its pharmaceutical acceptable salts.

The term "$(C_1-C_4)$alkyl" or "$(C_1-C_6)$alkyl" is understood as meaning a linear or branched hydrocarbon chain having 1 to 4 (respectively 6) carbon atoms such as for example a methyl, ethyl, propyl, isopropyl, butyl, isobutyl, tert-butyl, pentyl, isopentyl or hexyl radical.

The term "halo$(C_1-C_4)$- or $(C_1-C_6)$alkyl" is understood as meaning a $(C_1-C_4)$ or $(C_1-C_6)$alkyl radical in which 1 to 7 hydrogen atoms have been substituted with 1 to 7 halogen atoms such as for example a trifluoromethyl, a 2,2,2-trifluoroethyl, a pentafluoroethyl, a chloromethyl or a bromomethyl radical.

The term "halogen" is understood as meaning a chlorine, bromine, iodine or fluorine atom.

The term "$(C_3-C_8)$cycloalkyl" is understood as meaning a saturated monocyclic hydrocarbon having 3 to 8 carbon atoms such as for example a cyclopropyl, cyclobutyl, cyclopentyl, cyclohexyl, cycloheptyl or cyclooctyl radical.

The term "heteroaromatic radical" is understood as meaning a 5 or 6-membered monocyclic or 9 or 10-membered bicyclic aromatic heterocycles containing one or two heteroatoms chosen from N, S and O, such as for example a pyridinyl, pyridazinyl, pyrazinyl, pyrimidinyl, pyrazolyl, quinolinyl, isoquinolinyl, benzimidazolyl, benzoxazolyl, benzothiazolyl, indolyl or indazolyl radical.

Preferred compounds of formula (I) are those in which
$R^1$ is hydrogen, a $(C_1-C_6)$alkyl, a halo$(C_1-C_6)$alkyl or a phenyl;
$R^2$ is a $(C_3-C_8)$cycloalkyl; a phenyl optionally substituted by one or several substituents selected from the group consisting of a halogen, a $(C_1-C_4)$alkyl, a $(C_1-C_4)$alkoxy, a hydroxy, a nitro, a di$(C_1-C_4)$alkylamino, a $(C_1-C_4)$alkylsulfonylamino, a $(C_1-C_4)$alkylsulfonyl and a methylenedioxy; a phenyl$(C_1-C_4)$alkyl in which the phenyl is substituted by one or several substituents selected from the group consisting of a hydroxy, a $(C_1-C_4)$alkyl and a $(C_1-C_4)$alkoxy; or a 5- or 6-membered monocyclic aromatic heterocycle containing one or two nitrogen, sulfur and/or oxygen atoms;
$R^3$ is hydrogen or a halogen;
$R^4$ is a $(C_1-C_6)$alkyl, a $(C_1-C_4)$alkylcarbonylamino or an amino.

Especially preferred are the compounds of formula (I) in which $R^1$ is a $(C_1-C_4)$alkyl or a halo$(C_1-C_4)$alkyl such as trifluoromethyl.

Also especially preferred are the compounds of formula (I) in which $R^2$ is a phenyl optionally substituted by one or several substituents selected from the group consisting of a halogen, a $(C_1-C_4)$alkyl, a $(C_1-C_4)$alkoxy, a hydroxy, a nitro, a di$(C_1-C_4)$alkylamino, a $(C_1-C_4)$alkylsulfonylamino, a $(C_1-C_4)$alkylsulfonyl and a methylenedioxy.

Further especially preferred compounds of formula (I) are those in which $R^3$ is hydrogen and those in which $R^4$ is a $(C_1-C_6)$alkyl or an amino.

The following compounds are especially valuable:

1-(4-methoxy-phenyl)-3-methyl-5-(4-methylsulfonyl-phenyl)-1H-1,2,4-triazole 1-(4-methoxy-phenyl)-5-(4-methylsulfonyl-phenyl)-3-trifluoromethyl-1H-1,2,4-triazole 1-(4-bromo-phenyl)-5-(4-methylsulfonyl-phenyl)-3-trifluoromethyl-1H-1,2,4-triazole 1-(4-methylsulfonylamino-phenyl)-5-(4-methylsulfonyl-phenyl)-3-trifluoromethyl-1H-1,2,4-triazole 1-(4-methoxy-phenyl)-5-(4-aminosulfonyl-phenyl)-3-trifluoromethyl-1H-1,2,4-triazole.

The pharmaceutically acceptable salts of the compounds of formula (I) are non-toxic salts including (i) salts of compounds of formula (I) containing acidic groups, for example alkali metal salts or alkaline earth metal salts such as sodium salts, potassium salts, magnesium salts and calcium salts, and also salts with pharmaceutically acceptable quaternary ammonium ions or organic amines such as triethylamine, ethanolamine or tris-(2-hydroxyethyl)amine and the like, and (ii). salts of compounds of the formula (I) which contain basic groups, for example, salts with inorganic acids such as hydrochloric acid, hydrobromic acid, sulfuric acid, nitric acid, phosphoric acid and the like or with organic carboxylic acids such as acetic acid, propionic acid, glycolic acid, pyruvic acid, oxalic acid, malic acid, fumaric acid, tartaric acid, citric acid, benzoic acid, cinnamic acid, mandelic acid, methanesulfonic acid and the like.

The compounds of formula (I) are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, tendinitis, bursitis, burns, injuries, especially following surgical and dental procedure ID additi n, such compounds can inhibit cellular neoplastic transformations and metastasic tumor growth and hence can be used in the treatment of familial polyposis and cancer (colon, lung, oesophageal and gastric cancers). The compounds of formula (I) can also be useful for the treatment of dementia including pre-senile and senile dementia, and in particular, dementia associated with Alzheimer's disease (i.e. Alzheimer's dementia). The compounds of formula (I) also inhibit prostanoid-induced smooth muscle contraction by preventing the synthesis of contractile prostanoids and hence may be of use in the treatment of dysmenorrhea, premature labor and asthma.

By virtue of their high cyclooxygenase-2 (COX-2) inhibiting activity and/or their selectivity for inhibiting cyclooxygenase-2 over cyclooxygenase-1, the compounds of formula (I) prove useful as an alternative to conventional non-steroidal anti-inflammatory drugs (NSAIDs) particularly where such non-steroidal anti-inflammatory drugs may be contra-indicated such as in patients with peptic, ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptible to NSAID-induced asthma.

Accordingly, another object of this invention relates to the use of the compounds of formula (I) or their pharmaceutically acceptable salts for the preparation of a medicament intended for the treatment of cyclooxygenase-mediated diseases, especially those diseases susceptible to treatment with NSAIDs, and those advantageously treated by an agent which selectively inhibits COX-2 in preference to COX-1.

The invention also relates to a method of treating the above-mentioned cyclooxygenase-mediated diseases comprising the administration to a subject in need thereof of a therapeutically effective amount of a compound of formula (I) or a pharmaceutically acceptable salt thereof.

For the treatment of any of these cydooxygenase mediated diseases, the compounds of formula (I) may be administered, for example, orally, topically, parenterally, by inhalation spray or rectally in dosage unit formulations containing conventional non-toxic pharmaceutically acceptable carriers, adjuvants and vehicles. These dosage forms are given as examples, but other dosage forms may be developped by those skilled in the art of formulation, for the administration of the compounds of formula (I). The term parenteral as used herein includes subcutaneous injections, intravenous, intramuscular, intrasternal injection or infusion techniques. In addition to the treatment of humans, the compounds of formula (I) are useful in the treatment of warm-blooded animals such as mice, rats, horses, cattle sheep, dogs, cats, and the like.

A further object of this invention therefore relates to pharmaceutical compositions, comprising a therapeutically effective amount of a compound of formula (I) or a pharmaceutically acceptable salt thereof as the active ingredient The pharmaceutical compositions comprising the active ingredient may be in a form suitable for oral use, for example, as tablets, troches, lozenges, aqueous or oily suspensions, dispersible powders or granules, emulsions, hard or soft gelatin capsules, or syrups or elixirs. Compositions intended for oral use may be prepared according to any method known to the art for the manufacture of pharmaceutical compositions and such compositions may comprise one or more agents selected from the group consisting of sweetening agents, flavoring agents, coloring agents and preserving agents in order to provide pharmaceutically elegant and palatable preparations. Tablets comprise the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108, 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions comprise the active ingredient in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents such as a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitol monooleate. The aqueous suspensions may also comprise one or more preservatives, for example ethyl or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in a mineral oil such as liquid paraffin. The oily suspensions may comprise a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for the preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occuring phosphatides, for example soy bean, lecithin, and esters or partial esters derived from fatty acids and hexitol anhydrides, for example sorbitol monooleate, and condensation products of the said partial esters with ethylene oxide, for example polyoxyethylene sorbitol monooleate. The emulsions may also comprise sweetening and flavouring agents.

Syrups and elixirs may be formulated with sweetening agents, for example glycerol, propylene glycol, sorbitol or sucrose. Such formulations may also comprise a demulcent, a preservative and flavoring and coloring agents.

The pharmaceutical compositions may also be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents which may be employed water, Ringer's solution and an isotonic sodium chloride solution can be mentioned. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the active ingredient. These compositions can be prepared by mixing the active ingredient with a suitable non-irritating excipient which is solid at ordinary temperatures but liquid at the rectal temperature and will therefore melt in the rectum to release the active ingredient. Such materials are for example cocoa butter and polyethylene glycols.

For topical use, creams, ointments, jellies, solutions or suspensions, and the like, comprising a compound of formula (I) are employed (for the purpose of this application, topical application shall include mouth washes and gargles).

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the subject treated and the particular mode of administration. For example, a formulation intended for the oral administration in humans may comprise from 0.5 mg to 5 g of active ingredient compounded with an appropriate and convenient amount of carrier material which may vary from about 5 to about 95 weight percent of the total composition. Dosage unit forms will generally contain between from about 1 mg to about 1000 mg of active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The present invention further relates to processes for the preparation of the compounds of the formula (I). The compounds can be prepared by the sequences show below in reaction schemes I, II and III.

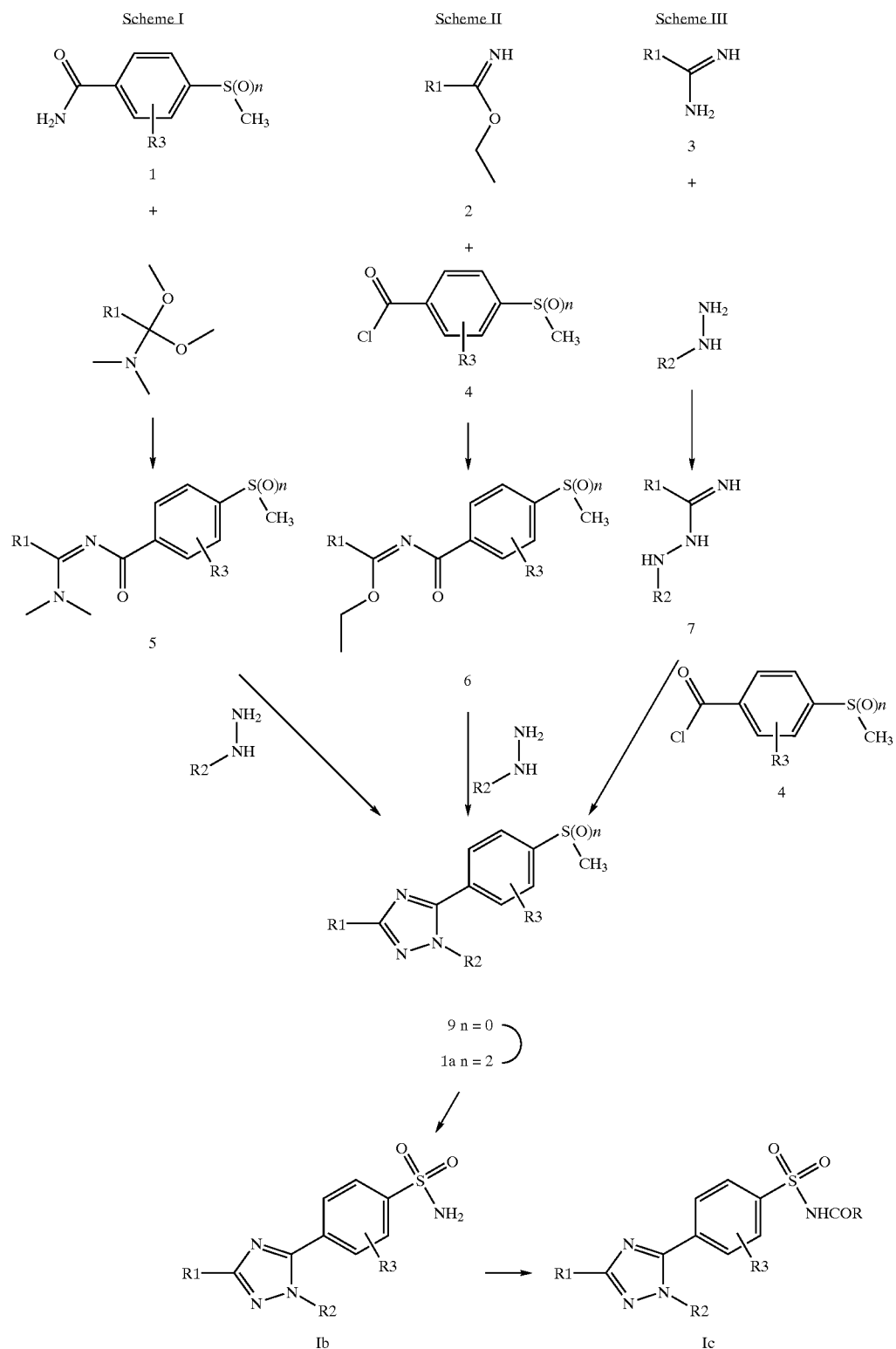

According to scheme I the starting materials can be amide derivatives of the formula I. They can be prepared from the corresponding carboxylic acids by processes described in the literature (for example see Org. Synth. col I, 153). Their condensation with N,N-dimethyl-amides dimethyl acetal, as described in Synthesis, 119 (1980), leads to the $N^2$-acyl-$N^1$, $N^1$-dimethylamidines 5. The condensation of the derivatives 5 with hydrazines in a polar solvent (e.g. methanol, ethanol or the like) yields the 1H-1,2,4-triazole compounds 9. One equivalent of an organic base is added if the hydrochloride salt of the hydrazine is used. The hydrazines are mainly commercially available or are prepared from the corresponding amines by methods known to those of ordinary skill in the art (Advanced organic chemistry, Jerry March, Wiley, 1985). Then oxidation with two equivalents of MCPBA in an inert solvent (e.g. chloroform) gives the 1H-1,2,4-triazole compounds Ia.

According to scheme II the starting materials can be alkylimidates 2 or their salts. The reaction of the alkylimidate with the benzoylchloride 4 in a presence of an organic base like triethylamine leads to the N-acylimidate 6. Such method is described in Synthesis, 483 (1983). The reaction is carried out at room temperature in a non polar solvent like methylene chloride, chloroform or toluene. The cyclisation of the N-acylimidate 6 with hydrazines to give the 1H-1,2,4-triazole compounds 9 takes place at room temperature without catalyst in a non polar solvent like methylene chloride. One equivalent of an organic base (like triethylamine) is added if the hydrochloride salt of the hydrazine is used. The oxidation step like in scheme I yields the 1H-1,2,4-triazole compounds Ia.

According to scheme III the starting materials can be amidine derivatives 3 or their salts. They are commercially available or can be prepared by processes described in the literature (G. V. BOYD, the chemistry of amidines and imidates, Wiley, vol 2, chapter 7, 339, 1991). The reaction of hydrazines with the amidine derivatives 3 is carried out at room temperature in a polar solvent (e.g. methanol or ethanol) yielding the amidrazones 7. The condensation of the amidrazones 7 with the benzoyl chloride 4 in the presence of an organic base like pyridine leads to 1H-1,2,4-triazole compounds 9. The reaction take place preferably at the reflux temperature of a non polar solvent like dioxane. The oxidation step like in scheme I yields the 1H-1,2,4-triazole compounds Ia.

The treatment of the arylmethylsulfones Ia with a base and triethylborane gives the corresponding rearranged sulfonic acids which are converted to the arylsulfonamides Ib during oxidative amination workup. Such method are described by H. Chuang, E. J. Reinhard and D. B. Reitz in Tetrahedron letters, 35 (39), 7201–7204, (1994). The arylmethylsulfones Ia are deprotonated with a small excess of a base like ethylmagnesium chloride at low temperature (e.g. 0° C.) in an inert solvent like THF and then are treated by triethylborane at the reflux temperature for several hours. Treatment with hydroxyamine-O-sulfonic acid at room temperature yields the arylsulfonamides Ib.

The sulfonamides Ib are treated with the acetyl chloride in acetic acid to give the acylsulfonamides Ic.

The invention will now be illustrated by the following examples and tests.

EXAMPLE 1

1-((3-chloro-4-methyl)-phenyl)-3-methyl-5-(4-methylsulfonyl-phenyl)-1H-1,2,4-triazole a) Ethyl N-(4-methylthio-benzoyl)-acetamidate To an ice-cool stirred suspension of ethyl acetamidate hydrochloride (80 g, 0.65 mol) and triethylamine (175 ml, 1.24 mol) in $CH_2Cl_2$ (1000 ml) was added dropwise a solution of 4-methylthio-benzoyl chloride (110 g, 0.591 mol) (prepared in situ from 4-methylthio-benzoic acid) in $CH_2Cl_2$. Then the reaction mixture was stirred overnight at room temperature. The organic layer was washed with water, dried with sodium sulfate and evaporated under vacuum. The resulting residue was chromatographed on silica gel using an 8/2 mixture of heptane/ethyl acetate as the eluent to give an amorphous solid (92 g, 65%). The compound was used for the next step without further purification.

$^1$H-NMR (DMSO $d_6$): 1.30 (t, J=7.2 Hz, 3H), 1.98 (s, 3H), 2.5 (s, 3H), 4.25 (q, J=7.2 Hz, 2H), 7.35 (dd, J=8.2 Hz, 2H), 7.85 (d, J=8.2 Hz, 2H).

b) 1-((3-chloro-4-methyl)-phenyl)-3-methyl-5-(4-methylthio-phenyl)-1H-1,2,4-triazole A solution of ethyl N-(4-methylthio-benzoyl)-acetamidate (5 g, 21.09 mmol), (3-chloro-4-methyl)-phenylhydrazine hydrochloride (4.5 g, 23.20 mmol) and triethylamine (3.5 ml, 25.31 mmol) in $CH_2Cl_2$ (2.5 ml) was stirred for 1.5 h at room temperature. The organic layer was washed with water, dried with sodium sulfate and evaporated under vacuum. The resulting residue was chromatographed on silica gel using an 8/2 mixture of toluene/ethyl acetate as the eluent to give a brown oil (6.4 g), which was crystallized from diisopropyl ether to afford a yellow orange powder (3.6 g, 52%) m.p. 100° C.

$^1$H-NMR ($CDCl_3$): 2.4 (s, 3H), 2.48 (s, 3H), 2.50 (s, 3H), 7.0–7.5 (m, 7H).

c) 1-((3-chloro-4-methyl)-phenyl)-3-methyl-5-(4-methylsulfonyl-phenyl)-1H-1,2,4-triazole To a solution of 1-((3-chloro-4-methyl)-phenyl)-3-methyl-5-(4-methylthio-phenyl)-1H-1,2,4-triazole (3.6 g, 10.9 mmol) in $CHCl_3$ (40 ml) were added 2 equivalents of MCPBA (6.3 g, 21.85 mmol). The reaction was stirred for 0.5 h at room temperature, then sodium hydrosulfite was added and the resulting mixture was neutralized with NaOH. The organic phase was separated, washed with saturated bicarbonate solution and dried over sodium sulfate. Evaporation under reduced pressure gave a light yellow oil (3.5 g). Crystallization from ethanol yielded a white solid (2.2 g, 56%) m.p. 156° C.

$^1$H-NMR ($CDCl_3$): 2.45 (s, 3H), 2.55 (s, 3H), 3.1 (s, 3H), 7.0 (dd, 1H), 7.3 (dd, 1H), 7.45 (d, 1H), 7.7 and 7.9 (AB, 4H).

The following compounds were obtained using the same procedure as in Example 1 but replacing the (3-chloro-4-methyl)-phenylhydrazine hydrochloride by:

4-fluoro-phenylhydrazine 4-chloro-phenylhydrazine 4-methyl-phenylhydrazine phenylhydrazine 2-chloro-phenylhydrazine 3-chloro-phenylhydrazine 4-tert-butyl-phenylhydrazine 4-bromo-phenylhydrazine 4-methoxy-phenylhydrazine 2,4-difluoro-phenylhydrazine 4-nitro-phenyl-hydrazine 3,4-difluoro-phenylhydrazine 3,4-dimethoxy-phenylhydrazine, and 4-dimethylamino-phenylhydrazine, respectively.

EXAMPLE 2

1-(4-fluoro-phenyl)-3-methyl-5-(4-methylsulfonyl-phenyl)-1H-1,2,4-triazole m.p. 180° C.

$^1$H-NMR ($CDCl_3$): 2.50 (s, 3H), 3.1 (s, 3H), 7.05–7.4 (m, 4H), 7.7 and 7.95 (AB, 4H).

MH+=332.

EXAMPLE 3

1-(4-chloro-phenyl)-3-methyl-5-(4-methylsulfonyl-phenyl)-1H-1,2,4-triazole m.p. 186° C.
$^1$H-NMR (CDCl$_3$): 2.50 (s, 3H), 3.1 (s, 3H), 7.30 and 7.45 (AB, 4H), 7.7 and 7.95 (AB, 4H).
MH+=348.

EXAMPLE 4

3-methyl-1-(4-methyl-phenyl)-5-(4-methylsulfonyl-phenyl)-1H-1,2,4-triazole m.p. 176° C.
$^1$H-NMR (CDCl$_3$): 2.4 (s, 3H), 2.5 (s, 3H), 3.05 (s, 3H), 7.2 (m, 4H), 7.7 and 7.9 (AB, 4H).

EXAMPLE 5

3-methyl-5-(4-methylsulfonyl-phenyl)-1-phenyl-1H-1,2,4-triazole m.p. 146° C.
$^1$H-NMR (CDCl$_3$): 2.5 (s, 3H), 3.05 (s, 3H), 7.25–7.5 (m, 5H), 7.7 and 7.9 (AB, 4H).

EXAMPLE 6

1-(2-chloro-phenyl)-3-methyl-5-(4-methylsulfonyl-phenyl)-1H-1,2,4-triazole m.p. 170° C.
$^1$H-NMR (CDCl$_3$) 2.5 (s, 3H), 3.05 (s, 3H), 7.4–7.6 (m, 4H), 7.7 and 7.9 (AB, 4H).

EXAMPLE 7

1-(3-chloro-phenyl)-3-methyl-5-(4-methylsulfonyl-phenyl)-1H-1,2,4-triazole m.p. 130° C.
$^1$H-NMR (CDCl$_3$): 2.5 (s, 3H), 3.05 (s, 3H), 7.15 (d, 1H), 7.25–7.50 (m, 2H), and 7.95 (AB, 2H).

EXAMPLE 8

1-(4-ter-butyl-phenyl)-3-methyl-5-(4-methylsulfonyl-phenyl)-1H-1,2,4-triazole m.p. 142° C.
$^1$H-NMR (CDCl$_3$): 1.35 (s, 9H), 2.55 (s, 3H), 3.1 (s, 3H), 7.25 and 7.45 (AB, 4H), 7.75 and 7.95 (AB, 4H).

EXAMPLE 9

1-(4-bromo-phenyl)-3-methyl-5-(4-methylsulfonyl-phenyl)-1H-1,2,4-triazole m.p. 188° C.
$^1$H-NMR (CDCl$_3$) 2.5 (s, 3H), 3.05 (s, 3H), 7.20 and 7.60 (AB, 4H), 7.70 and 7.95 (AB, 4H).

EXAMPLE 10

1-(4-methoxy-phenyl)-3-methyl-5-(4-methylsulfonyl-phenyl)-1H-1,2,4-triazole m.p. 128° C.
$^1$H-NMR (CDCl$_3$): 2.5 (s, 3H), 3.05 (s, 3H), 3.85 (s, 3H), 6.95 and 7.25 (AB, 4H), 7.7 and 7.9 (AB, 4H).

EXAMPLE 11

1-(2,4-difluoro-phenyl)-3-methyl-5-(4-methylsulfonyl-phenyl)-1H-1,2,4-triazole m.p. 160° C.
$^1$H-NMR (CDCl$_3$): 2.5 (s, 3H), 3.05 (s, 3H), 6.9–7.15 (m, 2H), 7.45–7.60 (m, 1H), 7.7 and 7.9 (AB, 4H).

EXAMPLE 12

3-methyl-5-(4-methylsulfonyl-phenyl)-1-(4-nitro-phenyl)-1H-1,2,4-triazole m.p. 180° C.
$^1$H-NMR (CDCl$_3$) 2.55 (s, 3H), 3.1 (s, 3H), 7.55 (d, 2H), 7.7 (d, 2H), 7.95 (d, 2H), 8.30 (d, 2H).

EXAMPLE 13

1-(3,4-difluoro-phenyl)-3-methyl-5-(4-methylsulfonyl-phenyl)-1H-1,2,4-triazole m.p. 194° C.
$^1$H-NMR (CDCl$_3$): 2.5 (s, 3H), 3.1 (s, 3.1H), 7.0–7.35 (m, 3H), 7.7 and 7.95 (AB, 4H).

EXAMPLE 14

1-(3,4-dimethoxy-phenyl)-3-methyl-5-(4-methylsulfonyl-phenyl)-1H-1,2,4-triazole m.p. 186° C.
$^1$H-NMR (DMSO d$_6$): 2.40 (s, 3H), 3.25 (s, 3H), 3.7 (s, 3H), 3.8 (s, 3H), 6.85 (dd, 1H), 7 (d, 1H), 7.1 (d, 1H), 7.7 and 7.95 (AB, 4H).

EXAMPLE 15

1-(4-dimethylamino-phenyl)-3-methyl-5-(4-methylsulfonyl-phenyl)-1H-1,2,4-triazole m.p. 200° C.
$^1$H-NMR (CDCl$_3$): 2.45 (s, 3H), 2.50 (s, 3H), 3.0 (s, 6H), 6.65 (d, 2H), 7.15 (2d, 4H), 7.45 (d, 2H).

EXAMPLE 16

1-(4-chloro-phenyl)-5-(4-methylsulfonyl-phenyl)-3-phenyl-1H-1,2,4-triazole a) Methyl N-(4-methylthio-benzoyl)-benzamidate To an ice-cool stirred suspension of methyl benzamidate hydrochloride (5.8 g, 33.8 mmol) and triethylamine (9 ml, 62.4 mmol) in CH$_2$Cl$_2$ (60 ml) was added dropwise a solution of 4-methylthio-benzoyl chloride (5.8 g, 30.7 mmol) (prepared in situ from 4-methylthio-benzoic acid) in CH$_2$Cl$_2$ (5.8 ml). Then the reaction mixture was stirred at room temperature. The organic layer was washed with water, dried with sodium sulfate and evaporated under vacuum. The resulting residue was chromatographed on silica gel using toluene as the eluent to give an amorphous solid (500 mg, 5%). The compound was used for the next step without further purification.

$^1$H-NMR (DMSO d$_6$): 2.5 (s, 3H), 4 (s, 3H), 7.3–7.6 (m, 7H), 7.9 (d, 2H).

b) 1-(4-chloro-phenyl)-5-(4-methylthio-phenyl)-3-phenyl-1H-1,2,4-triazole

A solution of methyl N-(4-methylthio-benzoyl)-benzamidate (500 mg, 1.75 mmol), (4-chloro)-phenylhydrazine hydrochloride (345 mg, 1.92 mmol) and triethylamine (0.3 ml, 2.1 mmol) in CH$_2$Cl$_2$ (2.5 ml) was stirred for 1.5 h at room temperature. The organic layer was diluted with dichloromethane, washed with water, dried with sodium sulfate and evaporated under vacuum. The resulting yellow solid was triturated with toluene to give a white solid (130 mg, 20%).

$^1$H-NMR (CDCl$_3$): 2.5 (s, 3H), 7.15–7.65 (m, 11H), 8.25 (dd, 2H).

c) 1-(4-chloro-phenyl)-5-(4-methylsulfonyl-phenyl)-3-phenyl-1H-1,2,4-triazole

To a solution of 1-(4-chloro-phenyl)-5-(4-methylthio-phenyl)-3-phenyl-1H-1,2,4-triazole (130 mg, 0.34 mmol) in CHCl$_3$ (5 ml) were added 2 equivalents of MCPBA (200 mg, 6.88 mmol). The reaction mixture was stirred for two days at room temperature, then sodium hydrosulfite was added and the resulting mixture was neutralized with concentrated NaOH. After extraction with chloroform, the organic phase was washed with water and dried over sodium sulfate. Evaporation under pressure and crystallization from ethanol yielded a white solid (50 mg, 36%) m.p. 170° C.

$^1$H-NMR (CDCl$_3$): 3.1 (s, 3H), 7.3–7.55 (m, 7H), 7.8 and 8.0 (AB, 4H), 8.15–8.30 (m, 2H).

EXAMPLE 17

1-(4-methoxy-phenyl)-5-(4-methylsulfonyl-phenyl)-3-trifluoromethyl-1H-1,2,4-triazole a) N-4-methoxy-phenyl)-trifluoroacetamidrazone A mixture of 4-methoxy-phenylhydrazine hydrochloride (27.84 g, 159.4 mmol), trifluoroacetamidine (2.5 g, 223.2 mmol), triethylamine (22.12 ml, 159.4 mmol) and methanol (100 ml) was stirred under nitrogen for 6 hours at room temperature. The reaction mixture was diluted with water (100 ml), extracted with ethyl acetate (3×100 ml), the combined organic layers were washed with water, saturated brine and dried over Na$_2$SO$_4$. Flash chromatography on silica gel (CH$_2$Cl$_2$ as the eluent) yielded a brown oil (3.5 g, 94%), which was used for the next step without further purification.

$^1$H-NMR (CDCl$_3$): 3.75 (s, 3H), 4.35 (bs, 2H), 6.1 (bs, 1H), 6.7 and 7.0 (AB, 4H).

b) 1-(4-methoxy-phenyl)-5-(4-methylthio-phenyl)-3-trifluoromethyl-1H-1,2,4-triazole To a solution of N-(4-methoxy-phenyl)-trifluoroacetamidrazone (3.5 g, 0.15 mol) and pyridine (11.6 ml) in dioxane (360 ml) was added a solution of 4-methylsulfonyl-benzoyl chloride (26.6 g, 0.142 mol) (prepared in situ from 4-methylthio-benzoic acid) in dioxane (120 ml). Then the reaction mixture was heated to reflux overnight. After evaporation of dioxane the residue was taken up in dichloromethane, the organic layer was washed with water, 0.1 N HCl, saturated brine, dried over sodium sulfate and evaporated under vacuum. The resulting residue was chromatographed on silica gel (CH$_2$Cl$_2$ as the eluent) to give a colorless oil (30.9 g, 65%).

$^1$H-NMR (DMSO d$_6$): 2.5 (s, 3H), 3.35 (s, 3H), 7.1 and 7.5 (AB, 4H), 7.3 and 7.4 (AB, 4H).

c) 1-(4-methoxy-phenyl)-5-(4-methylsulfonyl-phenyl)-3-trifluoromethyl-1H-1,2,4-triazole To a solution of 1-(4-methoxy-phenyl)-5-(4-methylthio-phenyl)-3-trifluoromethyl-1H-1,2,4-triazole (30 g, 0.08 mol) in CH$_2$Cl$_2$ (320 ml) was added portionwise MCPBA (47.2 g, 0.16 mol). The reaction mixture was stirred at room temperature for 1.5 h, then cooled to 0–5° C. and a sodium hydrosulfite solution (500 ml) was carefully added to maintain the temperature below 18–20° C. The pH was adjusted to 8 by the addition of NaOH 30%. The mixture was extracted with dichoromethane, the organic phase was washed with saturated brine, dried over sodium sulfate and evaporated. Flash chromatography on silica gel (toluene/ethyl acetate: 8/2 as the eluent) and recrystallization from ethanol yielded a white solid (29.42 g, 90%) m.p. 156° C.

$^1$H-NMR (DMSO d$_6$): 3.29 (s, 3H), 3.83 (s, 3H), 7.1 and 7.5 (AB, 4H), 7.75 and 8.0 (AB, 4H)

MH+=398.

EXAMPLE 18

1-(4-bromo-phenyl)-5-(4-methylsulfonyl-phenyl)-3-trifluoromethyl-1H-1,2,4-triazole a) N-(4-bromo-phenyl)-trifluoroacetamidrazone A mixture of 4-bromo-phenylhydrazine hydrochloride (7.1 g, 31.8 mmol), trifluoro-acetamidine (5 g, 44.6 mmol), triethylamine (4.5 ml, 31.8 nmol) and methanol (20 ml) was stirred overnight at room temperature. The reaction mixture was diluted with water, extracted with ethyl acetate, the organic layer was washed with water, saturated brine and dried over Na$_2$SO$_4$. Flash chromatography on silica gel (CH$_2$Cl$_2$ as the eluent) yielded an orange oil (6.7 g, 53%), which was used for the next step without further purification.

$^1$H-NMR (CDCl$_3$): 4.45 (bs, 2H), 6.25 (bs, 1H), 6.9 and 7.35–7.55 (AB, 4H).

b) 1-(4-bromo-phenyl)-5-(4-methylsulfonyl-phenyl)-3-trifluoromethyl-1H-1,2,4-triazole To a solution of N-(4-bromo-phenyl)-trifluoroacetamidrazone (6.7 g, 23.7 mmol) and pyridine (2.1 ml, 26.1 mmol) in dioxane (40 ml) was added a solution of 4-methylsulfonyl-benzoyl chloride (5.96 g, 27.3 mmol) prepared in situ from 4-methylsulfonyl-benzoic acid) in dioxane (40 ml). Then the reaction mixture was heated to reflux for 5 hours. After evaporation of dioxane the residue was taken up in dichloromethane, the organic layer was washed with water, 0.1 N HCl, saturated brine, dried over sodium sulfate and evaporated under vacuum. The resulting residue was chromatographed on silica gel using a 95/5 mixture of toluene/dioxane as the eluent, then recrystallized from ethanol to give a white solid (2.8 g, 26%).

m.p. 198° C.

$^1$H-NMR (DMSO d$_6$): 3.29 (s, 3H), 7.55 (d, 2H), 7.76 (d, 2H), 7.8 (dd, 2H), 8.02 (dd, 2H).

MH+=446.

The following compounds were obtained using the same procedure as in Example 18 but replacing the 4-bromo-phenylhydrazine hydrochloride by:

4-nitro-phenylhydrazine 4-fluoro-phenylhydrazine 4-chloro-phenylhydrazine cyclohexylhydrazine (prepared following N. I. Ghali, J. Org. Chem. 1981, 46, 5413), and 3,4-dimethoxy-phenyl-methyl-hydrazine, respectively.

EXAMPLE 19

1-(4-nitrophenyl)-5-(4-methylsulfonyl-phenyl)-3-trifluoromethyl-1H-1,2,4-triazole $^1$H-NMR (DMSO d$_6$): 3.30 (s, 3H), 7.85 (t, 4H), 8.05 (d, 2H), 8.45 (d, 2H).

EXAMPLE 20

1-(4-fluoro-phenyl)-5-(4-methylsulfonyl-phenyl)-3-trifluoromethyl-1H-1,2,4-triazole m.p. 230–232° C.

$^1$H-NMR (DMSO d$_6$): 3.27 (s, 3H), 7.4 (t, 2H), 7.6–7.8 (m, 2H), 7.8 and 8.0 (AB, 4H).

EXAMPLE 21

1-(4-chloro-phenyl)-5-(4-methylsulfonyl-phenyl)-3-trifluoromethyl-1H-1,2,4-triazole m.p. 190–192° C.

$^1$H-NMR (DMSO d$_6$): 3.3 (s, 3H), 7.2 (m, 4H), 7.8 and 8.05 (AB, 4H).

EXAMPLE 22

1-(cyclohexyl)-5-(4-methylsulfonyl-phenyl)-3-trifluoromethyl-1H-1,2,4-triazole m.p. 136° C.

$^1$H-NMR (DMSO d$_6$): 1.15–25 (m, 10H), 3.3 (s, 3H), 4.3–4.4 (m, 1H), 8 and 8.15 (AB, 4H).

EXAMPLE 23

1-(3,4-dimethoxy-phenyl-methyl)-5-(4-methylsulfonyl-phenyl)-3-trifluoromethyl-1H-1,2,4-triazole m.p. 142° C.

$^1$H-NMR (DMSO d$_6$): 3.3 (s, 3H), 3.7 (s, 3H), 5.5 (s, 2H), 6.9 and 7.1 (AB, 4H), 8 and 8.1 (AB, 4H).

The following compound was obtained using the same procedure as in Example 18 but replacing the 4-methylsulfonyl-benzoyl chloride by the 2-chloro-4-methylsulfonyl-benzoyl chloride and the 4-bromo-phenylhydrazine by the 4-methoxy-phenylhydrazine.

EXAMPLE 24

5-(2-chloro-4-methylsulfonyl-phenyl)-1-(4-methoxy-phenyl)-3-trifluoromethyl-1H-1,2,4-triazole m.p. 148° C.

$^1$H-NMR (DMSO d$_6$): 3.35 (s, 3H), 3.80 (s, 3H), 7 and 7.4 (AB, 4H), 8–8.2 (m, 3H).

EXAMPLE 25

1-(4-methylsulfonylamino-phenyl)-5-(4-methylsulfonyl-phenyl)-3-trifluoromethyl-1H-1,2,4-triazole a) 1-(4-amino-phenyl)-5-(4-methylsulfonyl-phenyl)-3-trifluoromethyl-1H-1,2,4-triazole A mixture of 1-(4-nitro-phenyl)-5-(4-methylsulfonyl-phenyl)-3-trifluoromethyl-1H-1,2,4-triazole (1.2 g, 2.91 mmol), iron powder (0.8 g, 14.27 mmol), ammonium chloride (0.80 g, 1.45 mmol), ethanol (25 ml) and water (13 ml) was heated to reflux for 1 hour, then cooled and filtered. The filtrate was poured onto water, extracted with ethyl acetate and a dichloromethane/methanol solution. The organic extracts were washed with saturated brine, dried over Na$_2$SO$_4$ and evaporated to give a yellow powder (1 g, 91%), which was used for the next step without further purification.

$^1$H-NMR (DMSO d$_6$): 3.30 (s, 3H), 5.7 (bs, 2H), 6.65 and 7.18 (AB, 4H), 7.75 and 8 (AB, 4H).

b) 1-(4-methylsulfonylamino-phenyl)-5-(4-methylsulfonyl-phenyl)-3-trifluoromethyl-1H-1,2,4-triazole To an ice-cool stirred suspension of 1-(4-amino-phenyl)-5-(4-methylsulfonyl-phenyl)-3-trifluoromethyl-1H-1,2,4-triazole (1 g, 2.61 mmol) and triethylamine (0.4 ml, 2.87 mmol) in CH$_2$Cl$_2$ (20 ml) was added dropwise methanesulfonylchloride (0.2 ml, 2.87 mmol). Then the reaction mixture was stirred at room temperature for 2 hours. TLC showed the presence of the starting material. Then 0.4 ml of methanesulfonylchloride and 10 mg of DMAP were added and the reaction mixture was heated to reflux for 2 hours. Again 0.4 ml of methanesulfonylchloride and 10 mg of DMAP were added and the mixture was stirred overnight at room temperature. The reaction mixture was diluted with water, extracted with CH$_2$Cl$_2$, the combined organic layers were washed with water, dried over Na$_2$SO$_4$ and evaporated to give a light yellow powder (1.1 g). The crude product was triturated with a mixture of dichloromethane/isopropyl ether to afford a beige solid (0.65 g). Then a solution of this solid in 60 ml of MeOH/THF (2/1) and 1N NaOH (3.6 ml) was stirred at room temperature for 0.25 h. After evaporation of the solvents, addition of ethyl acetate and neutralization with 1N HCl, the organic layer was washed with water, dried with sodium sulfate and evaporated. Crystallization from pentane and recrystallization from isopropyl ether/ethanol gave a light pink solid (0.3 g, 25%).

m.p. 188° C.

$^1$H-NMR (DMSO d$_6$): 3.15 (s, 3H), 3.30 (s, 3H), 7.35 and 7.55 (AB, 4H), 7.75 and 8.05 (AB, 4H).

MH+=461.

EXAMPLE 26

1,5-di-(4-methylsulfonyl-phenyl)-3-trifluoromethyl-1H-1,2,4-triazole a) N-(4-methylsulfonyl-phenyl)-trifluoroacetamidrazone A mixture of 4-(methylsulfonyl)-phenylhydrazine hydrochloride (10.1 g, 44.6 mmol), triethylamine (6.2 ml, 44.6 mmol), trifluoroacetamidine (2.5 g, 22.3 mmol), THF (40 ml) and methanol (40 ml) was stirred overnight at room temperature. The reaction mixture was diluted with water, extracted with ethyl acetate, the organic layer was washed with water, saturated brine and dried over Na$_2$SO$_4$. Flash chromatography on silica gel (cyclohexane/ethyl acetate: 8/2 as the eluent) and trituration from isopropyl ether yielded a solid (2.9 g, 46%) m.p. 164° C.

$^1$H-NMR (DMSO d$_6$): 3.1 (s, 3H), 6.7 (bs, 2H), 7.05 and 7.7 (AB, 4H), 9.25 (s, 1H).

b) 1,5-di-(4-methylsulfonyl-phenyl)-3-trifluoromethyl-1H-1,2,4-triazole

To a solution of N-(4-methylsulfonyl-phenyl)-trifluoroacetamidrazone (4.3 g, 15.28 mmol) and pyridine (1.4 ml, 16.8 mmol) in dioxane (30 ml) was added a solution of 4-methylsulfonyl-benzoyl chloride (4.3 g, 19.5 mmol) (prepared in situ from 4-methylsulfonyl-benzoic acid) in dioxane (10 ml). Then the reaction mixture was heated to reflux for 6 hours, then stirred overnight at room temperature. The reaction mixture was filtered, concentrated to dryness, partitioned between methylene chloride and water, the residue was extracted with methylene chloride, the organic layer was washed with 0.1 N HCl, saturated brine, dried over sodium sulfate and evaporated under vacuum. The resulting residue was chromatographed on silica gel using an 8/2 mixture of toluene/dioxane as the eluent, then recrystallized from ethanol to give a white solid (1.1 g, 26%) m.p. 214° C.

$^1$H-NMR (DMSO d$_6$): 3.29 (s, 3H), 3.32 (s, 3H), 7.8 (d, 2H), 7.9 (d, 2H), 8.03 (dd, 2H), 8.12 (dd, 2H).

MH+=446.

The following compounds were obtained using the same procedure as in Example 26 but replacing the 4-methylsulfonyl-phenyl hydrazine by:

3,4-dimethoxy-phenylhydrazine, and 3,4-methylenedioxy-phenylhydrazine, respectively.

EXAMPLE 27

1-(3,4-dimethoxy-phenyl)-5-(4-methylsulfonyl-phenyl)-3-trifluoromethyl-1H-1,2,4-triazole m.p. 140° C.
$^1$H-NMR (DMSO d$_6$): 3.25 (s, 3H), 3.7 (s, 3H), 3.8 (s, 3H), 7.1 (s, 2H), 7.28 (s, 1H), 7.8 and 8 (AB, 4H).

EXAMPLE 28

1-(3,4-methylenedioxy-phenyl)-5-(4-methylsulfonyl-phenyl)-3-trifluoromethyl-1H-1,2,4-triazole m.p. 185° C.
$^1$H-NMR (DMSO d$_6$): 3.30 (s, 3H), 6.2 (s, 2H), 7.1 (s, 2H), 7.28 (s, 1H), 7.8 and 8.05 (AB, 4H).

EXAMPLE 29

1-(4-hydroxy-phenyl)-5-(4-methylsulfonyl-phenyl)-3-trifluoromethyl-1H-1,2,4-triazole A mixture of 1-(4-methoxy-phenyl)-5-(4-methylsulfonyl-phenyl)-3-trifluoromethyl-1H-1,2,4-triazole (10 g, 25.2 mmol), 48% aqueous HBr (70 ml) and acetic acid (70 ml) was heated at 120° C. for 55 h. Then HBr 48% (20 ml) and AcOH (20 ml) were added and the mixture was heated again at 120° C. for 2 h. After cooling the solution was poured into water (2 l), the precipitate was filtered, washed several times with water and dried. Recrystallization from ethanol yielded a white solid (7.5 g, 78%).

m.p. 246° C.
$^1$H-NMR (DMSO d$_6$): 3.25 (s, 3H), 6.9 and 7.35 (AB, 4H), 7.75 and 8 (AB, 4H), 10.2 (bs, 1H).

EXAMPLE 30

1-(4-ethoxy-phenyl)-5-(4-methylsulfonyl-phenyl)-3-trifluoromethyl-1H-1,2,4-triazole A mixture of 1-(4-hydroxy-phenyl)-5-(4-methylsulfonyl-phenyl)-3-trifluoromethyl-1H-1,2,4-triazole (4 g, 10.4 mmol), KOH (1.5 g, 26.8 mmol) and DMF (40 ml) was stirred at room temperature for 1 h. Then diethylsulfate (1.6 ml, 12.2 mmol) was added, the reaction mixture stirred at room temperature for 13 h, NH$_4$OH (20 ml) added and the mixture poured into water (1 l). The precipitate was filtered, washed several times with water and dried. Recrystallization from ethanol yielded a white solid (3.7 g, 88%).

m.p. 112° C.
$^1$H-NMR (DMSO d$_6$): 1.35 (t, 3H), 3.3 (s, 3H), 4.10 (q, 2H), 7.1 and 7.5 (AB, 4H), 7.75 and 8 (AB, 4H).

EXAMPLE 31

1-(2-pyridinyl)-5-(4-methylsulfonyl-phenyl)-3-trifluoromethyl-1H-1,2,4-triazole hydrochloride a) N-(2-pyridinyl)-trifluoroacetamidrazone A mixture of 2-hydrazinopyridine (5 g, 45.8 mmol), trifluoroacetamidine (3.4 g, 30.5 mmol) and methanol (50 ml) was stirred overnight at room temperature. The reaction mixture was concentrated to dryness. Flash chromatography on silica gel (toluene/ethyl acetate: 65/35 as the eluent) gave a light orange amorphous solid (3.1 g, 50%), which was used for the next step without further purification.

$^1$H-NMR (DMSO d$_6$): 6.65 (bs, 3H), 7 (d, 1H), 7.1 (t, 1H), 8.05 (d, 1H), 9.2 (s, 1H).

b) 1-(2-pyridinyl)-5-(4-methylsulfonyl-phenyl)-3-trifluoromethyl-1H-1,2,4-triazole hydrochloride To a solution of N-(2-pyridinyl)-trifluoroacetamidrazone (3.1 g, 15.1 mmol) in dioxane (15 ml) was added a solution of 4-methylsulfonyl-benzoyl chloride (3.6 g, 16.7 mmol) (prepared in situ from 4-methylsulfonyl-benzoic acid) in dioxane (15 ml). Then the reaction mixture was refluxed for 2 hours. After cooling the reaction mixture was filtered and concentrated to dryness. The residue was chromatographed on silica gel using an 85/15 mixture of toluene/dioxane as the eluent, then recrystallized from ethanol to give a white solid (0.94 g, 15%).

m.p. 144° C.
$^1$H-NMR (DMSO d$_6$): 3.27 (s, 3H), 7.6 (t, 1H), 7.8 and 8 (AB, 4H), 7.9 (d, 1H), 8.16 (t, 1H), 8.46 (d, 1H).

The following compounds were obtained using the procedure of Example 31 but replacing the 2-hydrazinopyridine by:

3-hydrazinopyridine (prepared following WO97/10243), and 3-fluoro-4-methoxy-phenylhydrazine, respectively.

EXAMPLE 32

1-(3-pyridinyl)-5-(4-methylsulfonyl-phenyl)-3-trifluoromethyl-1H-1,2,4-triazole hydrochloride m.p 180° C.
$^1$H-NMR (DMSO d$_6$): 3.27 (s, 3H), 7.6 (m, 1H), 7.77 (d, 2H), 7.99–8.09 (m, 3H), 8.77 (s, 2H).

EXAMPLE 33

1-(3-fluoro-4-methoxy-phenyl)-5-(4-methylsulfonyl-phenyl)-3-trifluoromethyl-1H-1,2,4-triazole m.p. 180° C.
$^1$H-NMR (DMSO d$_6$): 3.30 (s, 3H), 3.95 (s, 3H), 7.35–7.5 (m, 2H), 7.65 (dd, 1H), 7.8 and 8.05 (AB, 4H).

EXAMPLE 34

1-(4-methoxy-phenyl)-5-(4-aminosulfonyl-phenyl)-3-trifluoromethyl-1H-1,2,4-triazole To an ice cooled solution of 1-(4-methoxy-phenyl)-5-(4-methylsulfonyl-phenyl)-3-trifluoromethyl-1H-1,2,4-triazole (10 g, 25.19 mmol) in THF (100 ml) was added dropwise a 2 M solution of n-butylmagnesium chloride in THF (21 ml, 42 mmol). Then the reaction mixture was stirred at room temperature for 3 h. The reaction mixture was cooled to 0° C., a 1 M solution of triethylborane in THF (70 ml, 70 mmol) was added dropwise and the reaction mixture was refluxed for 18 h. After cooling, a solution of hydroxylamine-O-sulfonic acid (12 g, 106 mmol) and sodium acetate (17.38 g, 210 mmol) in H$_2$O (140 ml) was added dropwise while maintaining the temperature below 15° C. Then the reaction mixture was stirred at room temperature for 2 h, the residue was extracted with ethyl acetate (2×100 ml), the organic layer was washed with saturated brine, dried over sodium sulfate and evaporated under vacuum. The resulting residue was chromatographed on silica gel using a 99/1 then 98/2 mixture of methylene chloride/methanol as the eluent, then recrystallized from ethanol to give a beige solid (2.5 g, 25%).

m.p. 228° C.
$^1$H-NMR (DMSO d$_6$): 3.9 (s, 3H), 7.15 (d, 2H), 7.5–7.6 (m, 4H), 7.75 and 7.95 (AB, 4H).

EXAMPLE 35

1-(4-methoxy-phenyl)-5-(4-(acetylamino)-sulfonyl)-phenyl-3-trifluoromethyl-1H-1,2,4-triazole To a suspension of 1-(4-methoxy-phenyl)-5-(4-(aminosulfonyl)-phenyl)-3-trifluoromethyl-1H-1,2,4- triazole (2 g, 5 mmol) in acetic acid (10 ml) was added dropwise acetyl chloride (10 ml). Then the reaction mixture was heated at 80° C. for 5 h, concentrated to dryness and the residue was chromatographed on silica gel using a 98/2 mixture of methylene chloride/methanol as the eluent, then recrystallized from a pentane/methanol mixture, to give a white solid (1.6 g, 72%).

m.p. 85° C.

$^1$H-NMR (CDCl$_3$): 2.05 (s, 3H), 3.9 (s, 3H), 7 and 7.3 (AB, 4H), 7.75 and 8.05 (AB, 4H).

EXAMPLE 36

1-(4-methoxy-phenyl)-5-(4-methylsulfonyl-phenyl)-1H-1,2,4-triazole a) N-(dimethylamino-methylene)-4-(methylsulfonyl)-benzamide A suspension of 4-methyl-sulfonyl-benzamide (8 g, 40.2 mmol) in dimethyl-formamide dimethyl acetal (16 ml, 120 mmol) was stirred at 120° C. for 1.75 h, during which time the formed methanol was collected through a reflux condenser. After cooling an orange solid was filtered and dried (8.92 g, 87%).

m.p. 130° C.

$^1$H-NMR (DMSO d$_6$): 3.16 (s, 3H), 3.22 (s, 3H), 3.27 (s, 3H), 8 and 8.35 (AB, 4H), 8.67 (s, 1H).

b) 1-(4-methoxy-phenyl)-5-(4-methylsulfonyl-phenyl)-1H-1,2,4-triazole

A mixture of N-(dimethylamino-methylene)-4-(methylsulfonyl)-benzamide (4 g, 15.7 mol), 4-methoxyphenylhydrazine hydrochloride (2.75 g, 15.7 mmol), triethylamine (2.2 ml, 15.7 mmol) in ethanol (20 ml) was heated to reflux for 25 h. After cooling, the reaction mixture was concentrated to dryness, then diluted with ethyl acetate. The organic phase was washed with water and saturated brine and dried over sodium sulfate. The residue was chromatographed on silica gel using a 70/30 mixture of toluene/dioxane as the eluent, then recrystallized from ethanol to give a light orange solid (0.4 g, 15%).

m.p. 182° C.

$^1$H-NMR (DMSO d$^6$): 3.26 (s, 3H), 3.82 (s, 3H), 7.05 and 7.35 (AB, 4H), 7.7 and 8 (AB, 4H), 8.3 (s, 1H).

Biological Tests Results

Example compounds according to the invention were tested for their ability to inhibit COX-1 and/or COX-2 activities in vitro. Purified COX-1 from ram seminal vesicles and purified COX-2 from ewe placenta (both from Cayman Chemicals) were incubated for 10 minutes at 25° C. in the presence of their substrate, arachidonic acid (5 µM), with or without test compounds or standard inhibitors. Prostaglandin E$_2$, the reaction product, was measured by enzymo-immunoassay (R&D Systems). Each individual value results from duplicate determinations. Final inhibition data are means±standard errors of at least (3) independent experiments performed on as many different days.

In this test system, diclofenac, a standard non selective inhibitor of both COX-1 and COX-2 reproducibly exerted its expected dose-related inhibitions of both COX-1 and COX-2 activities with IC$_{50}$ equal to 0.54±0.13 µM (17) and 0.97±0.14 µM (18), respectively. Nimesulide, a standard selective COX-2 inhibitor, was tested as a reference between 0.1 and 10 µM. At the intermediate concentration of 1 µM used for comparison, examples 3, 10, 15, 17, 18, 25 and 34 did not show any significant inhibition of COX-1, but were able to inhibit COX-2 selectively (Table 1).

TABLE 1

| Compound | (concentration) | % COX-1 inhibition (n) | % COX-2 inhibition (n) |
|---|---|---|---|
| Nimesulide | (0.1 µM) | +7 ± 6.6 (9) | −23 ± 5.4 (9) |
|  | (1 µM) | +16 ± 12.2 (26) | −30 ± 3.2 (23) |
|  | (10 µM) | +13 ± 8.3 (9) | −50 ± 5.4 (12) |
| Example 3 | (1 µM) | −2 ± 5.7 (6) | −19 ± 2.6 (3) |
| Example 10 | (1 µM) | −4 ± 14.6 (4) | −32 ± 4.5 (3) |
| Example 15 | (1 µM) | +2 ± 7.0 (3) | −18 ± 7 (3) |
| Example 17 | (1 µM) | +8 ± 2.7 (6) | −44 ± 6.8 (6) |
| Example 18 | (1 µM) | −5 ± 12 (3) | −53 ± 11 (3) |
| Example 25 | (1 µM) | −5 ± 9 (3) | −31 ± 10 (3) |
| Example 34 | (1 µM) | −16 ± 10 (3) | −78 ± 2 (3) |

(n) number of experiments

Examples 10 and 25 were of similar potency as nimesulide at the same concentration and examples 17, 18 and 34 were even more potent Example 18, one of the most potent compound in the series, appeared to be about 10 times more potent than nimesulide since it induced the same inhibition (−53%) as nimesulide (−50%) but at a 10 times lower concentration: 1 µM vs. 10 µM, respectively.

What is claimed is:
1. A compound of the formula (I)

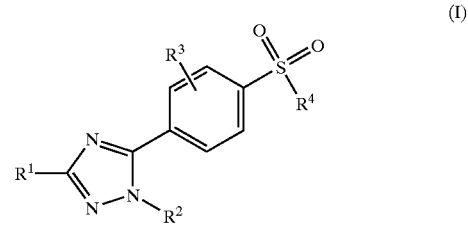

in which
R$^1$ is hydrogen; a (C$_1$–C$_6$)alkyl; a halo(C$_1$–C$_6$)alkyl; or a phenyl optionally substituted by one or several substituents selected from the group consisting of a (C$_1$–C$_4$)alkyl, a halogen, a halo(C$_1$–C$_4$)alkyl, a hydroxy, a (C$_1$–C$_4$)alkoxy, an amino, a mono- or di-(C$_1$–C$_4$)alkylamino, a (C$_1$–C$_4$)alkylcarbonylamino, a (C$_1$–C$_4$)alkylthiocarbonylamino, a (C$_1$–C$_4$)alkoxycarbonylamino, a (C$_1$–C$_4$)alkoxythiocarbonylamino, a (C$_1$–C$_4$)alkylsulfonyl, a (C$_1$–C$_4$)alkylsulfonylamino, a methylenedioxy, a nitro and a cyano;
R$^2$ is a (C$_1$–C$_6$)alkyl; a (C$_3$–C$_8$)cycloalkyl; a phenyl or a phenyl(C$_1$–C$_4$)alkyl in which the phenyl is optionally substituted by one or several substituents selected from the group consisting of a (C$_1$–C$_4$)alkyl, a halogen, a halo(C$_1$–C$_4$)alkyl, a hydroxy, a (C$_1$–C$_4$)alkoxy, an amino, a mono- or di-(C$_1$–C$_4$)alkylamino, a (C$_1$–C$_4$)alkylcarbonylamino, a (C$_1$–C$_4$)alkylthiocarbonylamino, a (C$_1$–C$_4$)alkoxycarbonylamino, a (C$_1$–C$_4$)alkoxythiocarbonylamino, a (C$_1$–C$_4$)alkylsulfonyl, a (C$_1$–C$_4$)alkylsulfonylamino, a methylenedioxy, a nitro and a cyano;
R$^3$ is hydrogen; a halogen; a hydroxy; a (C$_1$–C$_6$)alkoxy; an amino; a mono- or di-(C$_1$–C$_6$)alkylamino; a (C$_1$–C$_6$)alkylcarbonylamino; a (C$_1$–C$_6$)alkylthiocarbonylamino; a (C$_1$–C$_6$)alkoxycarbonylamino; a (C$_1$–C$_6$)alkoxythiocarbonylamino; a nitro; or a cyano;
R$^4$ is a (C$_1$–C$_4$)alkyl; an amino; a mono- or di-(C$_1$–C$_6$)alkylamino; a (C$_1$–C$_6$)alkylcarbonylamino; a (C$_1$–C$_6$)

alkylthiocarbonylamino; a $(C_1-C_6)$ alkoxycarbonylamino; or a $(C_1-C_6)$ alkoxythiocarbonylamino;

or a pharmaceutical acceptable salt thereof.

2. A compound according to claim 1, in which:

$R^1$ is hydrogen, a $(C_1-C_6)$alkyl, a halo$(C_1-C_6)$alkyl or a phenyl;

$R^2$ is a $(C_3-C_6)$cycloalkyl; a phenyl optionally substituted by one or several substituents selected from the group consisting of a halogen, a $(C_1-C_4)$alkyl, a $(C_1-C_4)$ alkoxy, a hydroxy, a nitro, a di$(C_1-C_4)$alkylamino, a $(C_1-C_4)$alkylsulfonylamino, a $(C_3-C_4)$alkylsulfonyl and a methylenedioxy; a phenyl$(C_1-C_4)$alkyl in which the phenyl is substituted by one or several substituents selected from the group consisting of a hydroxy, a $(C_1-C_4)$alkyl and a $(C_1-C_4)$alkoxy;

$R^3$ is hydrogen or a halogen;

$R^4$ is a $(C_1-C_4)$alkyl, a $(C_1-C_4)$alkylcarbonylamino or an amino;

or a pharmaceutically acceptable salt thereof.

3. A compound according to claim 1 in which $R^1$ is a $(C_1-C_4)$alkyl or a halo$(C_1-C_4)$alkyl, or a pharmaceutically acceptable salt thereof.

4. A compound according to claim 3 in which $R^1$ is trifluoromethyl, or a pharmaceutically acceptable salt thereof.

5. A compound according to claim 1 in which $R^2$ is a phenyl optionally substituted by one or several substituents selected from the group consisting of a halogen, a $(C_1-C_4)$ alkyl, a $(C_1-C_4)$alkoxy, a hydroxy, a nitro, a di$(C_1-C_4)$ alkylamino, a $(C_1-C_4)$alkylsulfonylamino, a $(C_1-C_4)$ alkylsulfonyl and a methylenedioxy;

or a pharmaceutically acceptable salt thereof.

6. A compound according to claim 1 in which $R^3$ is hydrogen, or a pharmaceutically acceptable salt thereof.

7. A compound according to claim 1 in which $R^4$ is a $(C_1-C_4)$alkyl or an amino, or a pharmaceutically acceptable salt thereof.

8. A compound or a pharmaceutically acceptable salt thereof which is selected from the group consisting of 1-(4-methoxyphenyl)-3-methyl-5-(4-methylsulfonylphenyl)-1H-1,2,4-triazole 1-(4-methoxyphenyl)-5-(4-methylsulfonylphenyl)-3-trifluoromethyl-1H-1,2,4-triazole 1-(4-bromophenyl)-5-(4-methylsulfonylphenyl)-3-trifluoromethyl-1H-1,2,4-triazole 1-(4-methylsulfonylamino-phenyl)-5-(4-methylsulfonylphenyl)-3-trifluoromethyl-1H-1,2,4-triazole 1-(4-methoxyphenyl)-5-(4-aminosulfonylphenyl)-3-trifluoromethyl-1H-1,2,4-triazole.

9. A pharmaceutical composition comprising a therapeutically effective amount of a compound of claim 1 or a pharmaceutically acceptable salt thereof, and a pharmaceutically acceptable carrier.

10. A pharmaceutical composition according to claim 9 comprising from 1 to 1000 mg of said compound.

11. The compound according to claim 2 in which $R^1$ is a $(C_1-C_4)$alkyl or a halo$(C_1-C_4)$alkyl, or a pharmaceutically acceptable salt thereof.

12. The compound according to claim 2 in which $R^2$ is a phenyl optionally substituted by one or several substituents selected from the group consisting of a halogen, a $(C_1-C_4)$ alkyl, a $(C_1-C_4)$alkoxy, a hydroxy, a nitro, a di$(C_1-C_4)$ alkylamino, a $(C_1-C_4)$alkylsulfonylamino, a $(C_1-C_4)$ alkylsulfonyl and a methylenedioxy;

or a pharmaceutically acceptable salt thereof.

13. The compound according to claim 11 in which $R^2$ is a phenyl optionally substituted by one or several substituents selected from the group consisting of a halogen, a $(C_1-C_4)$ alkyl, a $(C_1-C_4)$alkoxy, a hydroxy, a nitro, a di$(C_1-C_4)$ alkylamino, a $(C_1-C_4)$alkylsulfonylamino, a $(C_1-C_4)$ alkylsulfonyl and a methylenedioxy;

or a pharmaceutically acceptable salt thereof.

14. The compound according to claim 2 in which $R^3$ is hydrogen, or a pharmaceutically acceptable salt thereof.

15. The compound according to claim 5 in which $R^3$ is hydrogen, or a pharmaceutically acceptable salt thereof.

16. The compound according to claim 11 in which $R^3$ is hydrogen, or a pharmaceutically acceptable salt thereof.

17. The compound according to claim 2 in which $R^4$ is a $(C_1-C_4)$alkyl or an amino, or a pharmaceutically acceptable salt thereof.

18. The compound according to claim 5 in which $R^4$ is a $(C_1-C_4)$alkyl or an amino, or a pharmaceutically acceptable salt thereof.

19. The compound according to claim 6 in which $R^4$ is a $(C_1-C_4)$alkyl or an amino, or a pharmaceutically acceptable salt thereof.

20. The compound according to claim 11 in which $R^4$ is a $(C_1-C_4)$alkyl or an amino, or a pharmaceutically acceptable salt thereof.

21. A pharmaceutical composition comprising a therapeutically effective amount of a compound of claim 8 or a pharmaceutically acceptable salt thereof, and a pharmaceutically acceptable carrier.

22. The pharmaceutical composition according to claim 21 comprising from 1 to 1000 mg of said compound.

23. A method of treating inflammation in a mammal, which comprises administering to said mammal a therapeutically effective amount of a compound of claim 1 or a pharmaceutically acceptable salt thereof.

24. A method of treating inflammation in a mammal, which comprises administering to said mammal a therapeutically effective amount of a compound of claim 8 or a pharmaceutically acceptable salt thereof.

25. The compound according to claim 8 or a pharmaceutically acceptable salt thereof, which is 1-(4-methoxyphenyl)-5-(4-methylsulfonylphenyl)-3-trifluoromethyl-1H-1,2,4-triazole.

26. A pharmaceutical composition comprising a therapeutically effective amount of a compound of claim 25 or a pharmaceutically acceptable salt thereof, and a pharmaceutically acceptable carrier.

27. A method of treating inflammation in a mammal, which comprises administering to said mammal a therapeutically effective amount of a compound of claim 25 or a pharmaceutically acceptable salt thereof.

* * * * *